United States Patent [19]

Silber

[11] Patent Number: 5,476,455
[45] Date of Patent: Dec. 19, 1995

[54] TOXICITY RESISTANT TAMPON STRUCTURE

[76] Inventor: Arthur L. Silber, 543 Dobbins Ave., San Gabriel, Calif. 91775

[21] Appl. No.: 228,503

[22] Filed: Apr. 15, 1994

Related U.S. Application Data

[63] Continuation-in-part of Ser. No. 2,642, Jan. 11, 1993, Pat. No. 5,342,331.

[51] Int. Cl.$^6$ .............................. A61F 13/24; A61F 13/34
[52] U.S. Cl. ............................................ 604/330; 604/904
[58] Field of Search ................................ 604/330, 354, 604/904, 55; 128/769

[56] References Cited

U.S. PATENT DOCUMENTS

| | | |
|---|---|---|
| 1,996,242 | 4/1935 | Hagedorn . |
| 2,355,628 | 8/1944 | Calhoun . |
| 2,386,590 | 10/1945 | Calhoun . |
| 3,404,682 | 10/1968 | Waldron . |
| 3,491,758 | 1/1970 | Mullan . |
| 3,595,236 | 7/1971 | Corrigan et al. . |
| 3,626,942 | 12/1971 | Waldron . |
| 3,683,915 | 8/1972 | Voss . |
| 3,706,311 | 12/1972 | Kokx et al. . |
| 3,712,305 | 1/1973 | Wennerblom et al. . |
| 4,232,673 | 11/1980 | Bucalo . |
| 4,286,594 | 9/1981 | Cunningham . |
| 4,486,191 | 12/1984 | Jacob ...................................... 604/330 |
| 4,857,044 | 8/1989 | Lennon . |
| 5,342,331 | 8/1994 | Silber et al. ............................ 604/330 |

FOREIGN PATENT DOCUMENTS

| | | |
|---|---|---|
| 1123155 | 5/1982 | Canada . |
| 0753294 | 7/1956 | United Kingdom . |

Primary Examiner—David H. Willse
Attorney, Agent, or Firm—William W. Haefliger

[57] ABSTRACT

A flow-controlling tampon, comprising, in combination a generally upright insertion tube having upper and lower ends, and a plunger within said tube and manipulable proximate the tube lower end; flow receiving structure positioned within the tube to be bodily displaced and to protrude from the upper end of the tube in response to the manipulation of the plunger, the flow receiving structure having an upper end portion configured to expand to extend about the cervix in response to upward bodily displacement of the flow receiving structure effected by the plunger; and removal structure associated with the upper end portion of the receiving structure to effect contraction thereof when the receiving structure is withdrawn away from the cervix. The flow receiving structure typically includes flow absorbent material contained within a thin moisture resistant sheath having an expansible upper end that is contracted by pulling on strand structure.

17 Claims, 3 Drawing Sheets

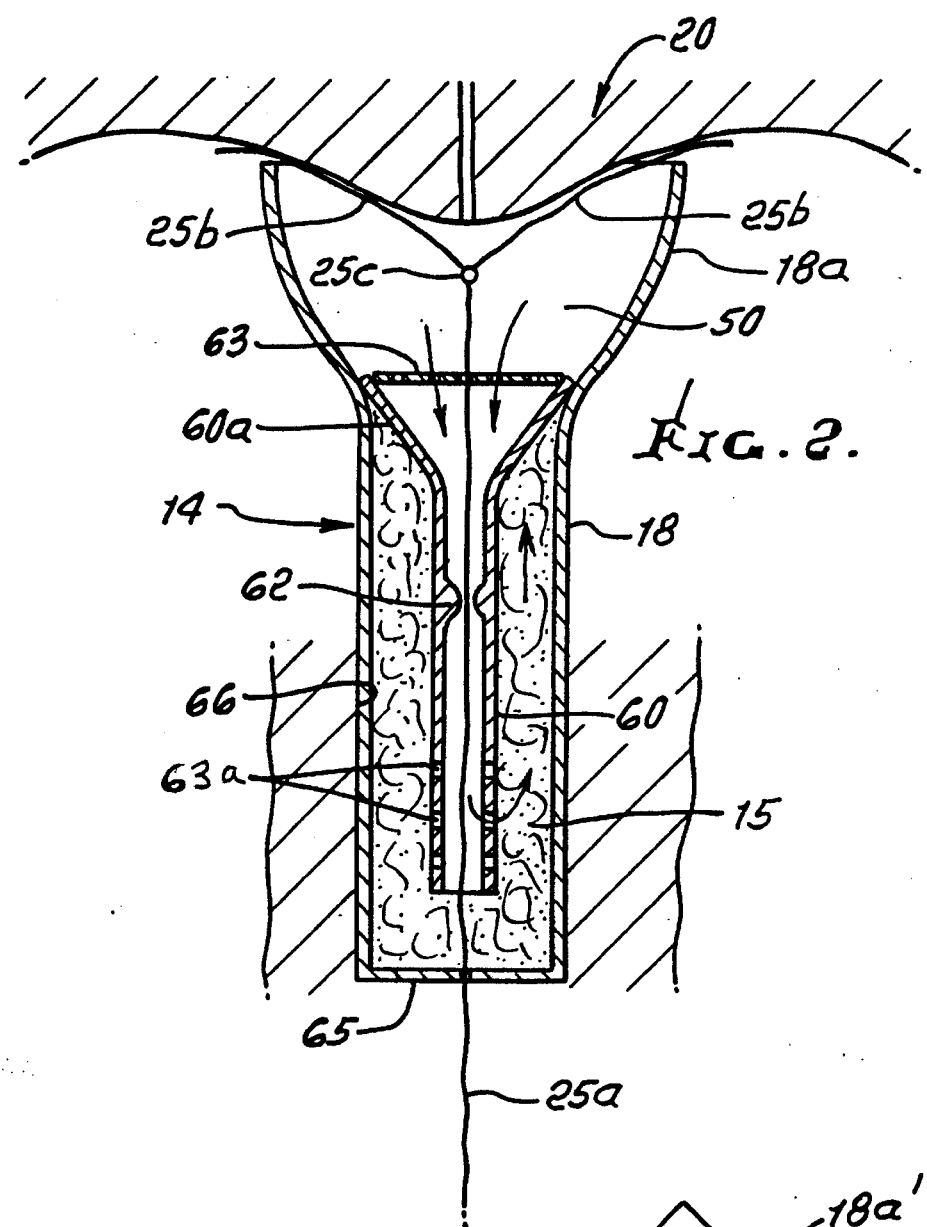
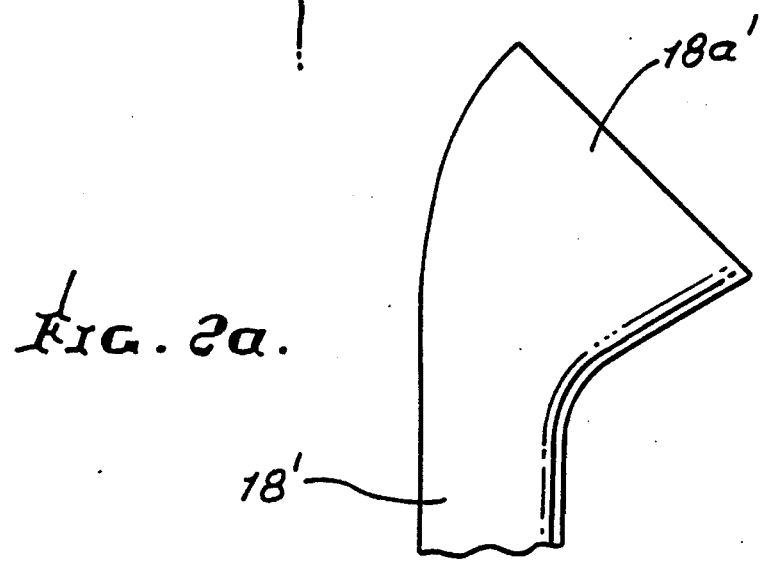

TOXICITY RESISTANT TAMPON STRUCTURE

This application is a continuation-in-part of Ser. No. 08/002,642 filed Jan. 11, 1993, now U.S. Pat. No. 5,342,331.

BACKGROUND OF THE INVENTION

This invention relates generally to flow-controlling tampons, and more specifically to an improved tampon which controls and collects menstrual flow in such manner as to prevent toxic reaction.

In the past, flow collection tampons were found to be objectionable due to toxic reaction, as at tissue surfaces contacted by the collecting flow or substances over periods of time. Also, prior tampons were found objectionable due to flow leakage and contact with the user's hands, as during tampon removal.

There is need for improved tampon apparatus overcoming the above problems and difficulties, as well as providing additional and improved structural and functional features, as well as enhanced or better results, including protection and comfort in use.

SUMMARY OF THE INVENTION

It is a major object to provide improved tampon apparatus which meets the above needs, by having no moisture absorbent area in direct contact with the user's body or mucosal membranes.

Basically, the flow-controlling tampon of the present invention comprises a flow-controlling tampon, comprising, in combination:

a) a generally upright, tube having upper and lower ends, and a plunger within said tube and manipulable proximate the tube lower end, b) flow receiving means positioned within the tube to be bodily displaced and to protrude from said upper end of the tube in response to said manipulation of the plunger, c) said flow receiving means having an upper end portion configured to expand to fit over the cervix in response to upward bodily displacement of said flow receiving means effected by the plunger, d) and removal means associated with said upper end portion of said receiving means to effect contraction thereof when said flow receiving means is withdrawn away from the cervix.

As will be seen, the flow receiving means may include a thin sheath typically extending about flow absorbent material, which is non-absorbent to said flow.

Another object is the provision of the expandable upper end of the flow receiving means to have cup shape, as when expanded. The cup may have funnel or scroll shape, or other shape allowing for expansion and contraction. Also, the flow absorbent material is typically fibrous and extends within the sheath to wick fluid upwardly, after flow down a central tube that receives flow from the upper cup.

A further object includes provision of the removal means to include a collapsible element interfitting the upper end portion of the flow receiving means. As will be seen, the collapsing element may include a string or flexible strand or strands to be pulled by force exerted during withdrawal of the flow absorbent means away from the cervix; and in this regard the pull strand may extend downwardly adjacent the flow absorbent means and away from said upper end portion of the sheath.

Yet another object includes the provision of lateral strands attached to said sheath upper portion, a main strand extending downwardly past the flow absorbent material, and a connection connecting said main strand and lateral strands. A pusher may be associated with said removal means to create withdrawal force pushing downwardly on the device when said removal means is displaced downwardly, manually, for extracting said tampon. The pusher is typically located to create such withdrawal force in conjunction with strand operation to at least partly close the flow collecting cup or sheath upper portion, as over a flow receiving pocket.

A further object includes the provision of a tampon device comprising:

a) flow receiving means adapted to be displaced toward the cervix, b) said flow receiving means including a moisture resistant sheath structure having an expansible upper portion to extend about the cervix, and also including flow absorbent material within the sheath structure, c) removal means associated with said upper end portion for collapsing same when the flow receiving means is withdrawn away from the cervix.

A further object is to provide a toxicity resistant device which has no moisture absorbent area in direct contact with the user's body or mucosal membranes.

These and other objects and advantages of the invention, as well as the details of an illustrative embodiment, will be more fully understood from the following specification and drawings, in which:

DRAWING DESCRIPTION

FIG. 2 is a view like FIG. 1 showing expansion of the upper end of the flow receiving means, to extend about the cervix, as during insertion;

FIG. 2a is an elevation showing a modified device;

DETAILED DESCRIPTION

Figure 1:
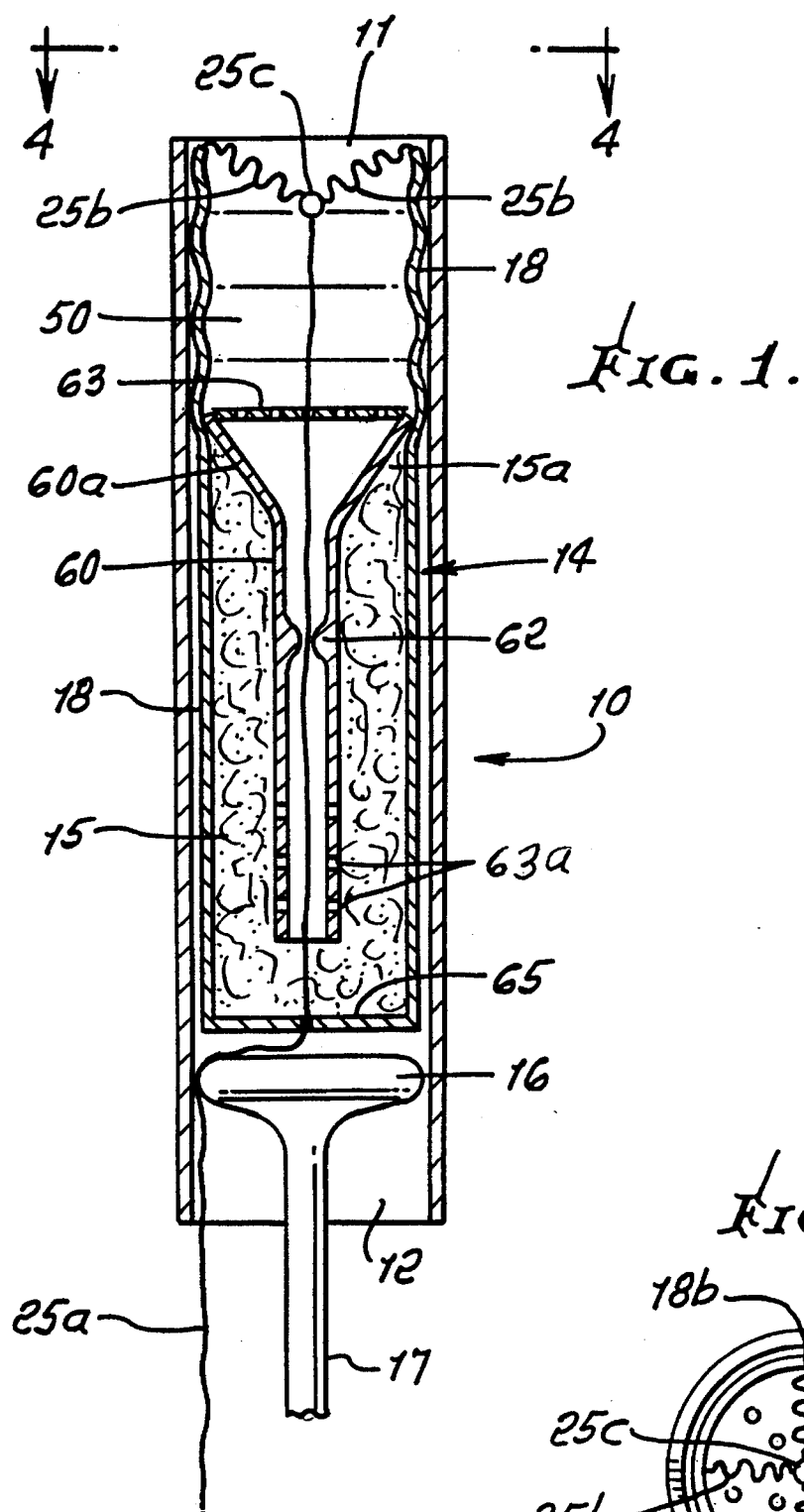
FIG. 1 is an elevation in section, to show one form of the invention, prior to expansion of the upper end of flow receiving means.

FIG. 1 shows a generally upright applicator tube 10 having an open upper end at 11 and an open lower end 12. The tube consists of fluid impervious plastic material, that prevents fluid passage through the tube wall. The tube is relatively stiff and non-collapsible enabling ready insertion within the vaginal passage.

Received within the tube is flow receiving means indicated at 14, to be bodily endwise displaced within and from the tube upper end. A plunger 16 within the tube and beneath the means 14 is adapted to be pushed upwardly via a stem 17, to expel the flow receiving means 14 endwise upwardly as referred to, after which the plunger and stem are retrieved. The flow receiving means includes a thin sheath 18 that extends about flow absorbing means 15, the sheath being impervious to moisture, whereby it does not collect moisture within the sheath wall, during use. The sheath may for example consist of latex.

The flow absorbing material 15 may be fibrous and packed together to form a fibrous body within the sheath. It has an upper end portion 15a just below the sheath upper end portion 18a, to be displaced from the tube 10, as effected by the plunger. Note also expansion of the sheath upper portion 18a to extend about the cervix 20. FIG. 2 shows this condition, with self-expanded wall bending upwardly and outwardly to encompass or bound the cervix when placed in position, by the plunger. The sheath may have "memory" to expand outwardly, as it is pushed out the upper end of the tube. Other modes of expansion are also possible, as for example outwardly expanded petals. Material 15 may have the same or similar composition as is used in conventional tampons.

Figure 4:
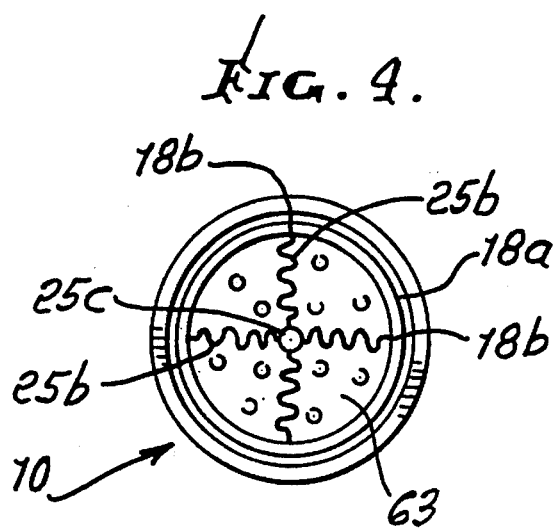
FIG. 4 is a section taken on lines 4—4 of FIG. 1.
Figure 6:
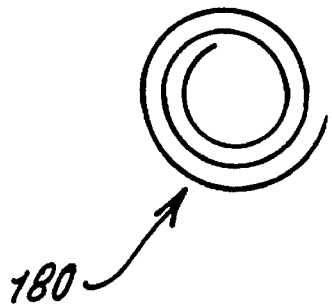
FIG. 6 is a view showing a scroll form of expansible flow absorption means.

The flow receiving means 14 is adapted to be readily removed, and also at least partially closed, upon manipulation of removal means associated with upper end portion or portions of 18, whereby the received flow is contained and held, i.e. not uncontrollably spilled. In FIGS. 1–4, the removal means takes the form of a string or flexible strand having a lower main strand section 25a, and upper strand sections 25b connected at 25c to 25a. The strand sections 25b are attached to the cup or cup sections 18b (if used) at or near their upper ends, and in such manner that when pulled, the strands 25a and 25b pull the cup sections toward one another to close the cup (see FIG. 3), thereby closing off the upper interior of the flow receiving sheath 18. Note flow receiving pocket 50 above material 15 to prevent fluid spillage upon retraction of the device away from the cervix. Note pull string section 25a extending downwardly alongside or through the absorbent material 15. Strand sections 25b are collapsed in FIG. 1, and extended in FIG. 2. FIG. 4 shows strand connections at 25d to uppermost extents of cup sections 18a. Pulling of string section 25a pulls the sections of the cup together with bowing as they are pulled downward, closing the pocket 50. See bowed extents 18e in FIG. 3. Such bowed extents can be pulled down into an inner flow tube 60, and in particular into the upper flared extent 60a of tube 60 (see FIG. 3). Note in FIG. 6 the alternative collapsible scroll shape of the collector 180 (substituted for 18a).

Figure 3:
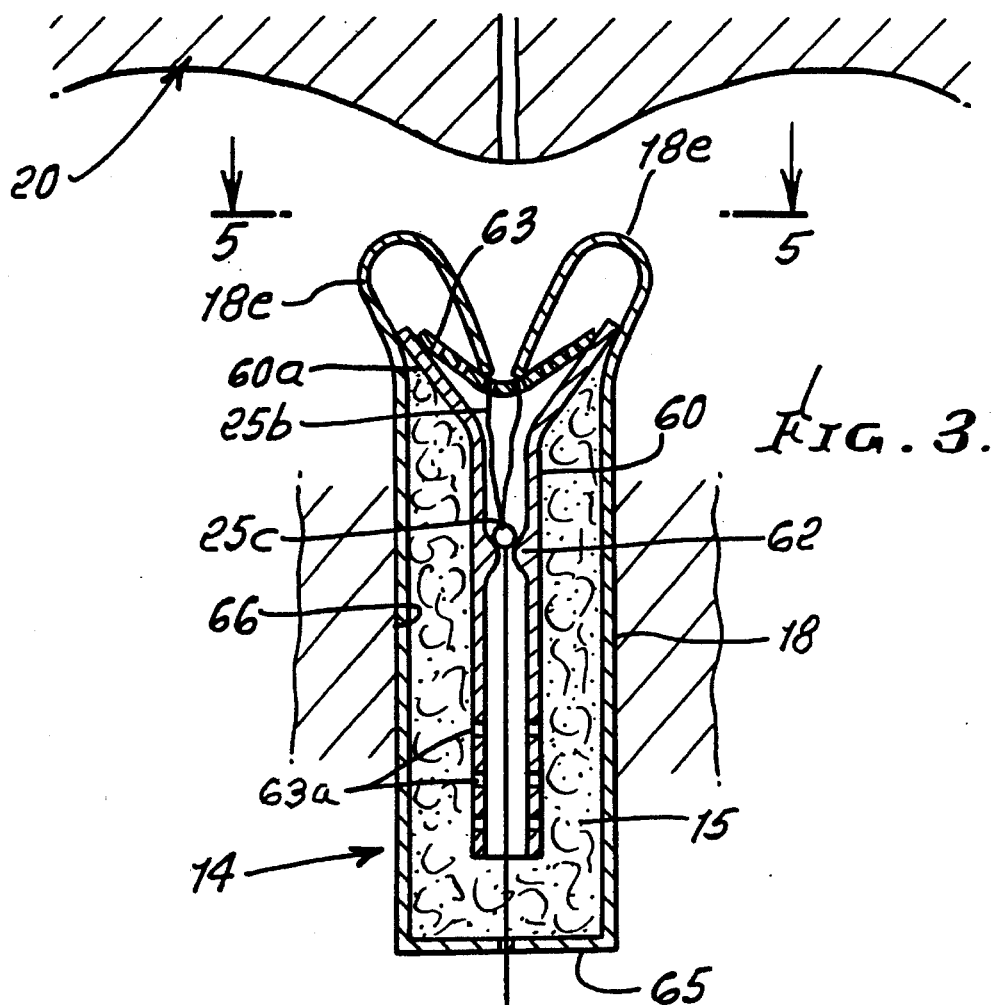
FIG. 3 is a view like FIG. 1, but showing the device during withdrawal away from the cervix.
Figure 5:
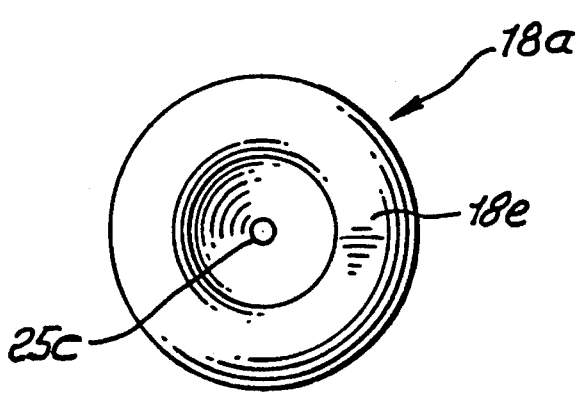
FIG. 5 is a section taken on lines 5—5 of FIG. 3.

The connection or knot 25c acts as a pusher, to push downward as seen in FIG. 3, to create withdrawal force to pull the tampon away from the cervix, during removal, in response to finger pulling downwardly on string 25a. Therefore the strands have the dual function of closing of the tampon pocket 50, as well as tampon removal, to prevent fluid spillage. The non-moisture absorbent quality of sheath 18 prevents toxicity, that might result from direct contact of fluid absorbent material with vaginal wall tissue.

Knot 25c may engage an annular obstruction 62 in tube 60, to create the downward force referred to. See FIG. 3. Tube 60 receives the flow from cup 18a, via a screen 63 extending across the upper flared extent 60a of tube 60. Flow clots are retained above that screen. Flow passing downwardly in inner tube 60 is then passed outwardly via perforations 63a, to wick upwardly in material 15, about inner tube 60, but within the sheath 18. The sheath lower end may be closed, at 15, as seen in FIG. 3. FIG. 3 also shows sheath retention in vaginal wall 66.

In FIG. 2a, the cup 18a' is angled relative to sheath 18' to conform more naturally to the anatomy.

The cup 18 may consist of biodegradable latex. The absorbent material may consist of a material such as laminaria hyperboria that forms a gel on aqueous flow contact.

As described this invention provides a device which has no moisture absorbent area in direct contact with the user's body or mucosal membranes.

I claim:

1. A flow-controlling tampon, for vaginal use comprising, in combination:
    a) a generally upright insertion tube having upper and lower ends, and a plunger within said tube and manipulable proximate the tube lower end,
    b) flow receiving means positioned within the tube to be bodily displaced and to protrude from said upper end of the tube in response to said manipulation of the plunger,
    c) said flow receiving means having an upper end portion configured to open to collector cup shape, conforming to the vestibule of the vagina, in response to upward bodily displacement of the entire flow receiving means as effected by the plunger,
    d) and removal means associated with said upper end portion of said receiving means to effect closure thereof as said flow receiving means is withdrawn from the vagina,
    e) said flow receiving means upper end portion being non-absorbent to the flow and having retained memory causing it to self-open outwardly into said cup-shape in response to its displacement upwardly from said tube, said upper end portion being free of connection to any auxiliary restraining means otherwise acting to pull it or form it into said cup-shape.

2. The combination of claim 1 wherein said flow receiving means includes flow absorbent material and a thin sheath about said flow absorbent material and which is non-absorbent to said flow.

3. The combination of claim 2 wherein said sheath consists of molded plastic material, and said upper and lower ends are open.

4. The combination of claim 2 including a stem attached to said plunger, and extending proximate said lower end of the tube, for pushing said plunger to expel said flow receiving means from the tube.

5. The combination of claim 2 including an internal tube extending downwardly within said sheath, to receive downward flow from said flow receiving means, and absorbent material about said internal tube to receive flow therefrom.

6. The combination of claim 5 wherein said upper end section of said flow receiving means forms a flow receiving pocket immediately above said flow absorbent material.

7. The combination of claim 5 wherein said removal means includes lateral strands attached to said flow receiving means, a main strand extending downwardly past said flow absorbent material, and a connection connecting said main strand and lateral strands, for pulling said flow receiving means downwardly toward and into said sheath, toward said flow absorbing material.

8. The combination of claim 7 including a pusher associated with said removal means to create withdrawal force pushing downwardly on said flow absorbent material when said removal means is displaced downwardly, manually, for extracting said tampon, said pusher positioned to be displaced downwardly to create said force in conjunction with said strands acting to at least partially close said sheath upper portions.

9. The combination of claim 1 wherein said upper end portion of said flow receiving means has cup configuration, when expanded.

10. The combination of claim 1 wherein said flow receiving means upper end portion is in collapsed condition prior to said upward bodily displacement thereof.

11. The combination of claim 1 wherein said removal means includes a collapsing element connected to said upper end portion of said flow receiving means.

12. The combination of claim 11 wherein said collapsing element includes flexible strand means to be pulled by force exerted during withdrawal of said flow receiving means away from the cervix.

13. The combination of claim 12 wherein said strand means includes a pull strand extending downwardly through said flow receiving means and away from said upper end portion of the flow receiving means.

14. The combination of claim 13 including an enlargement on said pull strand to be pulled downwardly and exert downward force on structure associated with said flow receiving means.

15. The combination of claim 1 including a pusher associated with said removal means to create withdrawal force pushing downwardly on said flow absorbent material when said removal means is displaced downwardly, manually, for extracting said tampon.

16. The combination of claim 1 wherein said upper end portion consists of biodegradable latex.

17. The combination of claim 1 wherein said upper end portion has one of the following shapes:
 i) petals
 ii) cup
 iii) scroll.

* * * * *